US008859709B2

(12) United States Patent
Katsoulis et al.

(10) Patent No.: US 8,859,709 B2
(45) Date of Patent: Oct. 14, 2014

(54) METHOD OF FORMING POLYHEDRAL OLIGOMERIC SILSESQUIOXANE COMPOUNDS

(75) Inventors: Dimitris Katsoulis, Midland, MI (US); Robert Thomas Larsen, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 13/996,696

(22) PCT Filed: Dec. 22, 2011

(86) PCT No.: PCT/US2011/066919
§ 371 (c)(1),
(2), (4) Date: Jun. 21, 2013

(87) PCT Pub. No.: WO2012/088448
PCT Pub. Date: Jun. 28, 2012

(65) Prior Publication Data
US 2013/0284973 A1 Oct. 31, 2013

Related U.S. Application Data

(60) Provisional application No. 61/426,068, filed on Dec. 22, 2010.

(51) Int. Cl.
*C08G 77/06* (2006.01)
*C08L 83/04* (2006.01)
*C08G 77/08* (2006.01)
*C07F 7/21* (2006.01)
*C08G 77/04* (2006.01)

(52) U.S. Cl.
CPC ............... *C08L 83/04* (2013.01); *C08G 77/08* (2013.01); *C07F 7/21* (2013.01); *C08L 2666/14* (2013.01); *C08G 77/045* (2013.01)
USPC .............................................. 528/19; 528/14

(58) Field of Classification Search
None
See application file for complete search history.

(56) References Cited

U.S. PATENT DOCUMENTS

| 2,629,725 | A | 2/1953 | Hyde |
| 4,670,299 | A | 6/1987 | Fukuyama et al. |
| 5,859,162 | A | 1/1999 | Yamamoto et al. |
| 5,973,095 | A | 10/1999 | Hacker et al. |
| 5,981,670 | A | 11/1999 | Itoh et al. |
| 6,281,285 | B1 | 8/2001 | Becker et al. |
| 6,395,825 | B1 | 5/2002 | Becker et al. |
| 6,399,733 | B1 | 6/2002 | Yamamoto et al. |
| 6,972,312 | B1 | 12/2005 | Lichtenhan et al. |
| 7,449,539 | B2 | 11/2008 | Morimoto et al. |

| 2005/0003215 | A1 | 1/2005 | Hacker et al. | |
| 2005/0239985 | A1* | 10/2005 | Lichtenhan et al. | 528/15 |
| 2009/0012317 | A1 | 1/2009 | Laine et al. | |

FOREIGN PATENT DOCUMENTS

| EP | 0516144 A1 | 5/1992 |
| JP | 06200030 A | 7/1994 |
| JP | 11322933 A | 11/1999 |
| JP | 2006249160 A | 9/2006 |
| JP | 2009138015 A | 6/2009 |
| JP | 2009191024 A | 8/2009 |
| JP | 2009263596 A | 11/2009 |
| RU | 2254346 C1 | 6/2005 |
| SU | 668280 A1 | 12/1981 |
| WO | WO 93/02126 A1 | 2/1993 |
| WO | WO 2010034161 A1 | 4/2010 |

OTHER PUBLICATIONS

English language abstract and Machine-Assisted English translation for JP 06200030 extracted from the PAJ database on Jan. 30, 2014, 14 pages.
English language abstract and Machine-Assisted English translation for JP 11322933 extracted from the PAJ database on Jan. 30, 2014, 39 pages.
English language abstract and Machine-Assisted English translation for JP 2006249160 extracted from the PAJ database on Jan. 29, 2014, 65 pages.
English language abstract and Machine-Assisted English translation for JP2 009138015 extracted from the PAJ database on Jan. 16, 2014, 61 pages.
English language abstract and Machine-Assisted English translation for JP 2009191024 extracted from the PAJ database on Jan. 29, 2014, 33 pages.
English language abstract and Machine-Assisted English translation for JP 2009263596 extracted from the PAJ database on Jan. 29, 2014, 65 pages. English language abstract for RU 2254346 extracted from the Espacenet.com database on Jan. 30, 2014, 9 pages.
English language translation for SU 668280 extracted from Google.com. Original document extracted from espacenet.com on Jan. 16, 2014, 5 pages.
English language abstract for WO 2010/034131 extracted from the Espacenet.com database on Jan. 29, 2014, 49 pages.
International Search Report for Application No. PCT/US2011/066919 dated Apr. 26, 2012, 4 pages.

(Continued)

*Primary Examiner* — Marc Zimmer
(74) *Attorney, Agent, or Firm* — Howard & Howard Attorneys PLLC

(57) ABSTRACT

A mixture of at least two polyhedral oligomeric silsesquioxane (POSS) compounds is formed in the presence of rhenium on cerium(IV) oxide. The POSS compounds are formed utilizing a method that includes the step of combining (a) a trihalosilane, (b) hydrogen gas, and (c) the rhenium on cerium(IV) oxide, in a reactor at a temperature of from 250° C. to 600° C. to form the mixture. The trihalosilane has the formula $RSiX_3$ wherein R is an alkyl group having from 1 to 4 carbon atoms, an aryl group, and wherein X is a halo atom. This method allows for the efficient, predictable, and accurate production of the POSS compounds with a minimized need for use of expensive separation techniques. In addition, this method produces the POSS compounds in commercially useful quantities as major reaction products thereby avoiding the need to run multiple reactions.

21 Claims, No Drawings

(56) References Cited

OTHER PUBLICATIONS

Bassindale, A.R. et al., "The Preparation of Hexasilsesquioxane (T6) Cages by 'Non Aqueous' Hydrolysis of Trichlorosilanes," Chem. Commun. 2003, pp. 1382-1383.

Duan, Qinghua, "Synthesis and Characterization of Ethoxy-Terminated Ladder-like Polymethylsilsesquioxane Oligomer," (2004), 53(1), pp. 113-120.

Guo, Zengchang, "Development in the Study on Synthesis of Polysilsesquioxanes," (2006) (1), pp. 16-27. With English abstract.

Huang, Chao, "Synthesis of Polymethylsesquisiloxane," (2003) 17(2), pp. 8-10. With English abstract.

Kamaritskii, B.A., "Synthesis of Oligoorganosilsesquioxanes and Their Properties," (1985), 1pp. 07-8. With English abstract.

Kireev, V.V., "Hydrolytic polycondensation of organochlorosilanes at the liquid-gas interface," (1986), 290(4), pp. 859-863. With English abstract.

Kudo, Takako, "Exploring the Mechanism for the Synthesis of Silsesquioxanes. 3. The Effect of Substituents and Water," Journal of Physical Chemistry A (2002, 106(46), pp. 11347-11353.

Lavrent'Ev, V.I., "Methylethyloctasilsesquioxanes as Products of the Reaction of Ethylpolycyclosiloxanes With Methyltrichlorosilane and Their Chromatographic-Mass Spectrometric Study," (1981), 51(1), pp. 124-130. With Englsih abstract.

Lichtenhan, J. "Silsesquioxane-Based Polymers," The polymeric Materials Encylopedia (1996).

Ma, Chenghuan, "Formation of Stable Nanoparticles of Poly(phenyl/methylsesquioxane) in Aqueous Solution," (2003), 35(3), pp. 270-275. With English abstract.

Martynova, T. N., "Feasibility of Directed Synthesis of Octa(Methyl, Vinyl) Silsesquioxanes," (1988), 61(2), pp. 418-421. With English abstract.

Qui, Jun, "Synthesis of Heat-Resisting Ladder Polymethylsilsesquioxane," (1999) 12(2), pp. 173-176. With English abstract.

Rabkina, A. Yu, "Formation of a Siloxane Bond Via Reactions of Chlorosilanes With Zinc Oxide in Aprotic Media," (2003), 45(4), pp. 562-571. With English abstract.

Ronchi, M. et al., "Fluoride catalyzed rearrangements of polysilsesquioxanes, mixed ME, vinyl T8, Me, vinyl T10 and T12 cages," Applied Organometallic Chemistry 2010, 24, 551-557.

Rosciszewski, Pawel, "Sythenses of Silsesquioxanes With Various Organic Substituents," (2006), 51(1), pp. 3-11. With English abstract.

Takiguchi, T. et al., "Preparation of Hexaphenylcyclotrisloxane by the Reaction of Diphenyldichlorosilane with Zinc Oxide," J. Org. Chem., vol. 25, No. 2, 1960, pp. 310-311.

Vasil'Eva, T.V., "Effect of Conditions for the Continuous Hydrolysis of Methyltrichlorosilane on the Composition of Reaction Products," (1981), (5), pp. 13-14. With English abstract.

Vasil'Eva, T.V., "Hydrolytic Polycondensation of Organotrichlorosilanes at a Liquid-Gas Interface," (1988), 30(3), pp. 487-491. With English abstract.

Wang, Da-xi, "Preparation of Phenyl/methyl Silsesquioxane High-Temperature Resistant Coating and its Properties," (2008) 22(6), pp. 353-356.

Wang, Da-xi, "Synthesis and Thermo-Stability Study of Ladderlike Phenyl/methyl Silsesquoxane Resin," (2009) 17(6), pp. 675-678. With English abstract.

Xie, B., "Repair and Capping of Porous MSQ Films Using Chlorosilanes and Supercritical CO2," (2005), 80, pp. 349-352.

Article: Xie, Zusho, "Study on the synthesis and characterization of the soluable, high molecular weight and ladderlike polymethylsilsesquioxane," Chinese Journal of Polymer Science (1989), 7(2), pp. 183-188.

* cited by examiner

METHOD OF FORMING POLYHEDRAL OLIGOMERIC SILSESQUIOXANE COMPOUNDS

RELATED APPLICATIONS

This application is the National Stage of International Patent Application No. PCT/US2011/066919, filed on Dec. 22, 2011, which claims priority to and all the advantages of U.S. Patent Application No. 61/426,068, filed on Dec. 22, 2010, the content of which is incorporated herein by reference.

FIELD OF THE INVENTION

The present invention generally relates to a method of forming polyhedral oligomeric silsesquioxane (POSS) compounds. More specifically, the method includes forming the POSS compounds in the presence of rhenium on cerium(IV) oxide.

DESCRIPTION OF THE RELATED ART

Silsesquioxanes are represented by the generic formula $(RSiO_{1.5})$ wherein each silicon atom is bound to an average of one and a half oxygen atoms (sesqui) and typically to one hydrocarbon group (ane). Silsesquioxanes are also known in the silicone arts to include "T" units wherein the generic formula is alternatively represented as $(RSiO_{3/2})$. The oxygen to silicon ratio of 1.5 (or 3/2) is intermediate between that found in silicones and silica, thus making silsesquioxanes hybrid compounds that have unique physical properties.

Silsesquioxanes are known to exist in various forms including in polyhedral oligomeric forms and in random three dimensional forms. In this form, the silsesquioxanes are typically referred to as polyhedral oligomeric silsesquioxane (POSS) compounds. POSS compounds are typically produced using hydrolysis/condensations reactions of trifunctional chlorosilanes (e.g. $RSiX_3$ wherein X is chloro) or alkoxysilanes. These reactions usually yield silsesquioxane resins as major products and POSS compounds as minor products or by-products such that fractional distillation processes must be used to isolate the POSS compounds in very small amounts. For this reason, it is very time consuming and expensive to generate POSS compounds in commercially useable multi-gram quantities. In addition, uncontrolled hydrolysis reactions of the aforementioned silanes do not typically form POSS compounds with predictability or regularity. For these reasons, there remains an opportunity to develop an improved and more efficient method for forming POSS compounds.

SUMMARY OF THE INVENTION AND ADVANTAGES

The instant invention provides a method of forming a mixture of at least two polyhedral oligomeric silsesquioxane (POSS) compounds in the presence of rhenium on cerium (IV) oxide. The method includes the step of combining (a) a trihalosilane, (b) hydrogen gas, and (c) the rhenium on cerium (IV) oxide, in a reactor at a temperature of from 250° C. to 600° C. to form the mixture. The (a) trihalosilane has the formula $RSiX_3$ wherein R is an alkyl group having from 1 to 4 carbon atoms or an aryl group and wherein X is a halo atom.

This method allows for the efficient, predictable, and accurate production of POSS compounds with a minimized need for use of expensive separation techniques. Perhaps more importantly, this method produces POSS compounds in commercially useful quantities as major reaction products thereby avoiding the need to utilize multiple reactions. Further, this method can preferentially form particular POSS compounds, if desired, thereby further minimizing costs and production times.

DETAILED DESCRIPTION OF THE INVENTION

The present invention provides a method of forming a mixture of at least two polyhedral oligomeric silsesquioxane (POSS) compounds. The POSS compounds of the mixture, and of this invention as a whole, are not particularly limited to any chemical or structural form. Typically, POSS compounds are crystalline solids that are sublimable under vacuum and that have a wide range of melting points and decomposition temperatures near or exceeding about 400° C. However, inclusion and/or variation of organic groups in the POSS compounds can change their physical properties.

In one embodiment, one or more of the POSS compounds has a symmetrical, fully condensed silicon-oxygen framework with organic functionality on each silicon atom, such as those shown below in structures (I)-(IV):

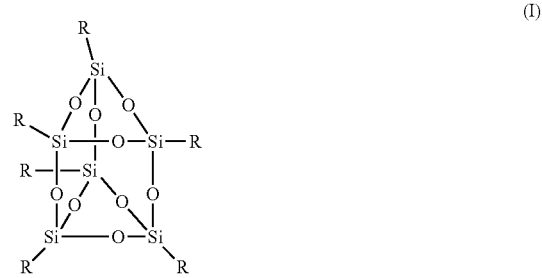

(I)

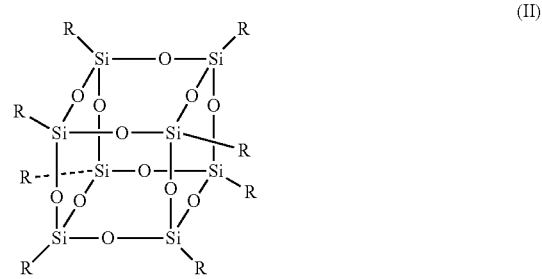

(II)

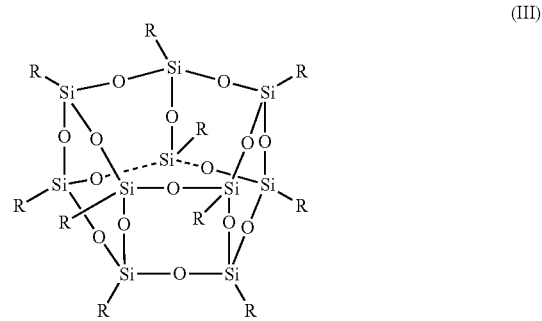

(III)

-continued

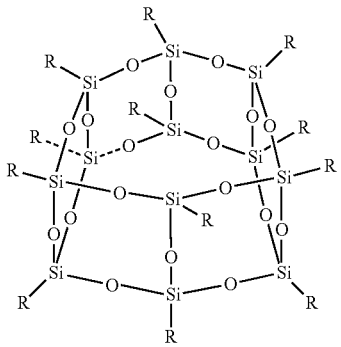
(IV)

In another embodiment, one or more of the POSS compounds has an incompletely condensed framework, such as those shown below in structures (V)-(VIII):

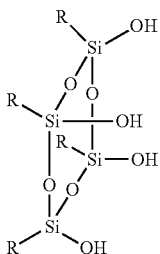
(V)

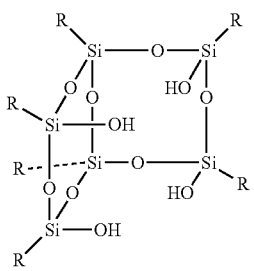
(VI)

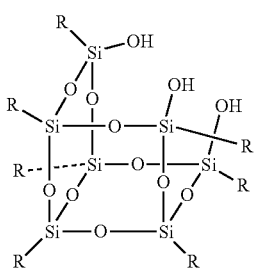
(VII)

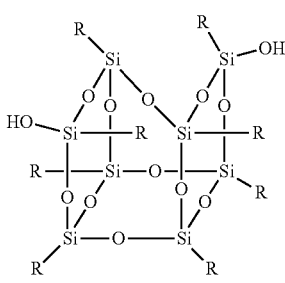
(VIII)

In still other embodiments, one or more of the POSS compounds has a completely condensed framework while one or more additional POSS compounds has an incompletely condensed framework. Condensation reactions of hydroxy groups in the developing POSS compounds can drive the reaction to near completion producing volatile POSS compounds that can be isolated.

It is also contemplated that each of the at least two POSS compounds may independently have the formula $(RSiO_{1.5})_n$ wherein R is an alkyl group having from 1 to 4 carbon atoms or an aryl group and n is 6, 8, 10, and/or 12. Typically, a POSS compound that has the formula $(RSiO_{1.5})_6$ has a structure that approximately corresponds to structures (I) or (VI) above. A POSS compound that has the formula $(RSiO_{1.5})_8$ has a structure that approximately corresponds to structures (II) or (VIII) above. A POSS compound that has the formula $(RSiO_{1.5})_{10}$ has a structure that approximately corresponds to structure (III) above. A POSS compound that has the formula $(RSiO_{1.5})_{12}$ has a structure that approximately corresponds to structure (IV) above. It is contemplated that n may alternatively be 4 or 7, as generally illustrated in structures (V)-(VIII) above.

Most typically one or more R groups in the POSS compounds is further defined as a methyl group. In one embodiment, each of the at least two POSS compounds have the formula $(RSiO_{1.5})_n$ wherein R is a methyl group and n is 6, 8, 10, or 12. Alternatively, each of the at least two POSS compounds may have the formula $(RSiO_{1.5})_n$ wherein R is alkyl group having from 1 to 4 carbon atoms and n is 6, 8, 10, or 12. Further, at least one POSS compound may have the formula $(RSiO_{1.5})_n$ wherein R is an alkyl group having from 1 to 4 carbon atoms and n is 6, 8, 10, or 12.

It is contemplated that the mixture may consist of, or consist essentially of, two or three, four, five, six (or more) POSS compounds. In various embodiments, the terminology "consisting essentially of" refers to the mixture being free of unreacted trihalosilanes and/or incompletely condensed POSS compounds. Alternatively, the terminology "consisting essentially of" may refer to the mixture including less than 1, 0.5, 0.1, or 0.01 parts by weight of unreacted trihalosilanes and/or incompletely condensed POSS compounds. In still other embodiments, the mixture may be free of, or includes less than 1, 0.5, 0.1, or 0.01 parts by weight of, condensed POSS compounds. In one particular embodiment, the mixture consists essentially of three POSS compounds wherein each POSS compound independently has the formula $(RSiO_{1.5})_n$ and wherein n is 6 for a first POSS compound, 8 for a second POSS compound, and 10 for a third POSS compound.

Method of Forming the Mixture:

Referring back to the method more specifically, the method typically includes the steps of providing each of (a) a trihalosilane (b) hydrogen gas, and (c) rhenium on cerium(IV) oxide. These elements (a)-(c) can be formed and/or provided by any means known in the art. Typically, the (a) trihalosilane is a liquid at room temperature. However, the (a) trihalosilane is typically provided as a gas, e.g. through use of a carrier gas and a bubbler that includes the (a) trihalosilane. The (b) hydrogen gas ($H_2$) may be of any purity but typically has a purity of greater than 90, 95, or 99, percent. Typically, the (c) rhenium on cerium(IV) oxide is solid and is provided as particles (i.e., in particulate form). One or more of (a), (b), and/or (c) may be provided in a single amount or may be provided in sequential steps, over a period of time, in a series of smaller amounts. In other words, (a), (b), and (c) may be provided in a first amount and the method may also include adding a supplemental amount of (a), (b), and/or (c). Typically, supplemental amounts of (a), (b), and/or (c) are added after the initial step of providing and/or combining.

Trihalosilane:

The (a) trihalosilane may be any known in the art having the formula $RSiX_3$ wherein R is an alkyl group having from 1 to 4 carbon atoms or an aryl group and wherein X is a halo atom. Typically, the (a) trihalosilane is further defined as $CH_3SiCl_3$, $CH_3SiBr_3$, or combinations thereof. Alternatively, mixtures of (a) trihalosilanes may be utilized to customize the POSS compounds formed in this invention. For example, combinations of $CH_3SiCl_3$ and $CH_3SiBr_3$ may be utilized independently or in conjunction with $CH_3CH_2SiCl_3$ and/or $CH_3CH_2SiBr_3$.

Rhenium on Cerium(IV) Oxide:

In the method of this invention, the mixture of the at least two POSS compounds is typically formed in the presence of the (c) rhenium on cerium(IV) oxide, also referred to as $Re/CeO_2$. In other words, the at least two POSS compounds themselves are formed in the presence of the (c) rhenium on cerium(IV) oxide.

The (c) rhenium on cerium(IV) oxide acts as a catalyst for forming the POSS compounds. The rhenium is typically disposed on the cerium(IV) oxide, which acts as a solid support for the rhenium. The cerium(IV) oxide may lose oxygen atoms during formation of the POSS compounds but can be regenerated by exposure of cerium(III) oxide to diatomic oxygen ($O_2$) (or atmospheric air) to re-gain an oxygen atom (and reform cerium(IV) oxide), thereby regenerating the catalyst. In addition, any cerium oxychloride (CeOCl) that is produced during formation of the POSS compounds may also lose chlorine atoms to reform cerium(IV) oxide and also regenerate the catalyst.

The (c) rhenium on cerium(IV) oxide may be formed by any method known in the art. In one embodiment, the (c) rhenium on cerium(IV) oxide is formed by dissolving $ReCl_3$ in isopropyl alcohol to form a solution. The solution is then added to $CeO_2$ powder by an incipient wetness technique. The powder is then vacuum dried. Moreover, the particular amount or weight percent of the rhenium on the cerium(IV) oxide is not particularly limited. Typically, the rhenium is present in an amount of from 0.01 to 10, of from 0.1 to 5, or from 0.5 to 3, weight percent based on the cerium(IV) oxide. Of course, the invention is not limited to these weight percents or ranges and the weight percent of the rhenium on the cerium(IV) oxide may be any value or range of values, both whole and fractional, within those ranges and values described above. It is also contemplated that the weight percent may vary from the values and/or range of values above by ±5%, ±10%, ±15%, ±20%, ±25%, ±30%, etc.

The method may also include the step of regenerating the cerium(IV) oxide. As set forth in the reaction scheme above, the method may include the step of exposing cerium(III) to diatomic oxygen ($O_2$) and/or to atmospheric air to reform cerium(IV) oxide. Alternatively, the method may include the step of treating the cerium oxychloride (CeOCl) such that it loses chlorine atoms to reform cerium(IV) oxide. These steps may occur sequentially or simultaneously and may occur in conjunction with each other or independently.

Additional Method Steps:

The method also includes the step of combining (a), (b), and (c) in a reactor at a temperature of from 250° C. to 600° C. to form the mixture. In other words, the method includes the step of combining (a), (b), and (c) to react in the reactor and form the mixture of at least two POSS compounds. The following reaction (or a similar analog) may occur in the reactor:

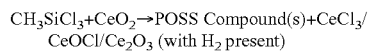
$CH_3SiCl_3 + CeO_2 \rightarrow$ POSS Compound(s) $+ CeCl_3/$
CeOCl/$Ce_2O_3$ (with $H_2$ present)

As described above, the $CeCl_3/CeOCl/Ce_2O_3$ may be treated or used in a one or more steps to regenerate the cerium(IV) oxide.

In various embodiments, the temperature of the reactor is from 260 to 590, from 270 to 580, from 280 to 570, from 290 to 560, from 300 to 550, from 310 to 540, from 320 to 530, from 330 to 520, from 340 to 510, from 350 to 500, from 360 to 490, from 370 to 480, from 380 to 470, from 390 to 460, from 400 to 450, from 410 to 440, or from 420, to 430, ° C. The invention is not limited to any of the aforementioned temperatures and any one or more of those temperatures may be further defined as a particular temperature or range of particular temperatures, both whole and fractional, within those ranges described above. It is also contemplated that any one or more of the aforementioned temperatures or temperature ranges may vary by ±5%, ±10%, ±15%, ±20%, ±25%, ±30%, etc.

The reactor may operate in a continuous, semi-continuous, or batch mode or in a combination of modes. Alternatively, two or more reactors can be used, each independently operating in a continuous, semi-continuous, or batch mode or its own combination of modes. In one example, a first reactor is used to react (a), (b), and (c), and a second reactor is used to generate (and/or regenerate) the cerium(IV) oxide. In this example, one or both of these reactors can be operated in a continuous mode. The particular type of reactor is not limited and may be further defined as a fluidized bed reactor, a gas phase heterogeneous reactor, a fixed bed reactor, etc. The length and size of the reactor are also not particularly limited as the reactor may be a laboratory scale reactor or an industrial scale reactor. In various embodiments, the length of the reactor (in laboratory scale) is from 3 to 8 cm with a volume of from 1 to 5 cm$^3$. An industrial scale reactor may have similar length and volume proportions or those proportions may be different.

In one embodiment, the (c) rhenium on cerium(IV) oxide is stationary and the (a) trihalosilane and (b) hydrogen gas are passed through and/or over the (c) rhenium on cerium(IV) oxide. In laboratory scale, the (a) trihalosilane and/or (b) hydrogen gas typically has a residence time in or over the (c) rhenium on cerium(IV) oxide of from 0.1 to 10, from 0.5 to 10, from 0.5 to 9.5, from 1 to 8.5, from 1.5 to 8, from 2 to 7.5, from 3 to 7, from 3.5 to 6.5, from 4 to 6, from 4.5 to 5.5, or of about 5, seconds. An industrial scale reactor or reaction may utilize residence times in similar proportions from those described above or those proportions may be different. It is contemplated that the (a) trihalosilane and (b) hydrogen gas can react for a time of from minutes to hours. In other words, the entire reaction (and not any one particular residence time) typically occurs for a time of from minutes to hours. In various embodiments, (a), (b), and (c), react for a time of from 1 to 60 minutes, from 1 to 40 minutes, from 1 to 20 minutes, from 1 to 24 hours, from 1 to 15 hours, from 1 to 10 hours, from 1 to 5 hours, etc. In addition, (a), (b), and (c) tend to react to form the mixture having POSS compounds present in amounts of at least 1, 2, 3, 4, 5, 10, 15, 20, 25, 30, etc. weight percent. In various embodiments, the mixture has POSS compounds present in amounts of greater than 50, 60, 70 80, 90, or 95, weight percent.

Each of (a), (b), and (c), typically react at atmospheric pressure or higher but this invention is not limited to any particular pressure. In various embodiments, the pressure is further defined as 0.5, 1, 1.5, 2, 2.5, 3, 3.5, 4, 4.5, 5, or 5+, atmospheres. The invention is not limited to any of the aforementioned values and any one or more of those values may be further defined as a particular value or range of particular values, both whole and fractional, within those ranges described above. It is also contemplated that any one or more of the aforementioned values or ranges may vary by ±5%, ±10%, ±15%, ±20%, ±25%, ±30%, etc.

After formation of the mixture, the method may further include one or more of the steps of removing the mixture from the reactor, removing one or more POSS compounds from the reactor, and/or separating one or more of the POSS compounds from the mixture. Typically, the mixture is removed from the reactor before separation of the POSS compounds. However, one or more of the POSS compounds may be removed from the reactor independently from a remainder of the mixture. One or more of the POSS compounds may be separated from the mixture by any means known in the art including chromatography, distillation, sublimation, etc.

Additional Embodiments

This invention also provides a method of forming the mixture including at least three POSS compounds. In this embodiment, each POSS compound independently has the formula $(RSiO_{1.5})_n$, wherein R is as described above, and wherein n is 6 for a first POSS compound, 8 for a second POSS compound, and 10 for a third POSS compound. In a similar embodiment, R may be $CH_3$. The mixture may consist essentially of the three POSS compounds. In this embodiment, the terminology "consisting essentially of" is as described above. The instant invention also provides the mixture itself, as described above. The mixture and/or the POSS compounds themselves can be used in a variety of applications.

EXAMPLES

A mixture of POSS compounds was formed according to the instant invention along with a series of comparative examples. The mixture of POSS compounds was compared to the comparative examples to demonstrate the superior and unexpected results of this invention.

Example 1

Formation of Mixture of POSS Compounds of This Invention

The (c) rhenium on cerium(IV) oxide was prepared by dissolving 0.1025 g $ReCl_3$ (Sigma Aldrich, 99+%) in 8.8 mL of isopropyl alcohol to form a solution. The solution was then added to $CeO_2$ powder by an incipient wetness technique wherein enough solution was added to 2.0679 g $CeO_2$ (Sigma Aldrich, 99%) to just wet the entire mass of powder such that any more solution would not be taken up by the powder. The wet powder was then vacuum dried at 80° C. for 4 hours to yield a powder including 2 wt % of rhenium on the cerium (IV) oxide powder.

After formation, 0.60 g of the (c) rhenium on cerium(IV) oxide powder was then loaded into a quartz glass tube and placed in a flow reactor and purged with $H_2$. Activation of the catalyst was performed with 100 sccm $H_2$ (controlled via Omega FMA 5500 mass flow controller) at 500° C. for ~2 hours (heated in a Lindberg/Blue Minimite 1" tube furnace). Reaction was then initiated by bubbling 100 sccm of $H_2$ through a stainless steel $MeSiCl_3$ bubbler (wherein Me is methyl) that was held at 23° C. The gas and vapor leaving the bubbler were passed into the reactor. The bubbler was designed with sufficient contact time such that the $MeSiCl_3$ vapor was in equilibrium with the gases leaving the bubbler, and as such, the flow rate of $MeSiCl_3$ leaving the bubbler could be determined by well known thermodynamic relationships. The reaction was periodically sampled over the course of 60 min by GC/GC-MS to monitor the amounts of various reaction products. The effluent of the reactor passed through an actuated 6-way valve (Vici) with constant 100 μL injection loop before being discarded. Samples were taken from the reaction by actuating the valve and a 100 μL sample passed directly into an injection port of a 7890A Agilent GC-MS for analysis with a split ratio at the injection port of 100:1. The GC included two 30 m SPB-Octyl columns (Supelco, 250 um inner diameter, 0.25 um thick film), which were disposed in parallel such that the sample was split evenly between the two columns. One column was connected to a TCD detector for quantification of the reaction products and the other column was connected to a mass spectrometer (Agilent 7895C MSD) for sensitive detection of trace products and positive identification of any products that formed. Instead of being heated in a GC oven, the columns were heated using an Agilent LTM module. In other words, the columns were wrapped with heating elements and thermocouples such that they were precisely and rapidly ramped to desired temperatures. This low thermal mass system allowed rapid analysis (7-10 minutes) between sample injections.

In this Example, the reaction products produced were almost exclusively cage structured methyl silsesquioxanes including 6, 8, or 10 corner shared Si atoms and edge shared O atoms, denoted as $Me-T_6$, $Me-T_8$, and $Me-T_{10}$. The reaction produced small to moderate amounts of these $Me-T_n$ structures for about 30-40 minutes before the catalyst was depleted. If the catalyst was exposed to air at 500° C. for 1 hour to replenish depleted O atoms from the $CeO_2$ support and then activated with $H_2$ and reacted with $H_2$ and $MeSiCl_3$ in the manner described above, it could again have been used to produce more $Me-T_n$ products.

Comparative Example 1

In Comparative Example 1, $H_2$ and $MeSiCl_3$ were reacted in the presence of $CeO_2$ (without any Re present) under the same conditions as described above. GC-MS confirmed that no POSS compounds (i.e., $Me-T_n$ structures) were formed.

Comparative Example 2

In Comparative Example 2, $H_2$ and $MeSiCl_3$ were reacted in the presence of 2 wt % rhenium on $Al_2O_3$ powder (without any $CeO_2$ present) under the same conditions as described above. Yet again, GC-MS confirmed that no POSS compounds (i.e., $Me-T_n$ structures) were formed.

Comparative Example 3

In Comparative Example 3, $H_2$ and $MeSiCl_3$ were reacted in the presence of 2 wt % rhenium on $TiO_2$ powder (without any $CeO_2$ present) under the same conditions as described above. GC-MS confirmed that no POSS compounds (i.e., $Me-T_n$ structures) were formed.

The results set forth above indicate that the instant invention efficiently, predictably, and accurately produces POSS compounds. Moreover, the results indicate that rhenium on cerium(IV) oxide produces superior and unexpected results when compared to other similar catalysts, as described in the comparative examples.

The invention has been described in an illustrative manner, and it is to be understood that the terminology which has been used is intended to be in the nature of words of description rather than of limitation. Many modifications and variations of the present invention are possible in light of the above teachings, and the invention may be practiced otherwise than as specifically described.

It is to be understood that the appended claims are not limited to express any particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

What is claimed is:

1. A method of forming a mixture comprising at least two polyhedral oligomeric silsesquioxane (POSS) compounds in the presence of rhenium on cerium(IV) oxide, said method comprising the step of combining (a) a trihalosilane, (b) hydrogen gas, and (c) the rhenium on cerium(IV) oxide in a reactor at a temperature of from 250° C. to 600° C. to form the mixture, wherein the (a) trihalosilane has the formula $RSiX_3$, R is an alkyl group having from 1 to 4 carbon atoms or an aryl group, and X is a halo atom.

2. A method as set forth in claim 1 wherein each of the at least two POSS compounds is fully condensed.

3. A method as set forth in claim 1 wherein each of the at least two POSS compounds independently has the formula $(RSiO_{1.5})_n$ wherein R is an alkyl group having from 1 to 4 carbon atoms and n is 6, 8, 10, or 12.

4. A method as set forth in claim 1 wherein at least one POSS compound has the formula $(RSiO_{1.5})_n$ wherein R is an alkyl group having from 1 to 4 carbon atoms and n is 6, 8, 10, or 12.

5. A method as set forth in claim 1 wherein at least one POSS compound has the formula $(RSiO_{1.5})_n$ wherein R is a methyl group and n is 6, 8, 10, or 12.

6. A method as set forth in claim 1 wherein the mixture consists essentially of three POSS compounds wherein each POSS compound independently has the formula $(RSiO_{1.5})_n$ wherein R is an alkyl group having from 1 to 4 carbon atoms and wherein n is 6 for a first POSS compound, 8 for a second POSS compound, and 10 for a third POSS compound.

7. A method as set forth in claim 1 wherein the trihalosilane is further defined as $CH_3SiCl_3$.

8. A method as set forth in claim 1 further comprising the step of separating one of the POSS compounds from the mixture via sublimation.

9. A method as set forth in claim 1 further comprising the step of reactivating the rhenium on cerium(IV) oxide after the mixture is formed.

10. A method as set forth in claim 9 wherein the step of reactivating occurs in a second reactor.

11. A method as set forth in claim 1 further comprising the step of adding an additional amount of the rhenium on cerium (IV) oxide to the reactor after the step of combining.

12. A method as set forth in claim 1 wherein the process is further defined as continuous and the reactor is further defined as a fluidized bed reactor.

13. A method as set forth in claim 1 wherein the reactor is operated at a pressure that exceeds atmospheric pressure.

14. A method as set forth in claim 1 further comprising the step of removing the POSS compounds from the reactor.

15. A method as set forth in claim 1 wherein the mixture comprises at least three polyhedral oligomeric silsesquioxane (POSS) compounds, wherein the (a) trihalosilane is further defined as $CH_3SiCl_3$, wherein each POSS compound independently has the formula $(CH_3SiO_{1.5})_n$, and wherein n is 6 for a first POSS compound, 8 for a second POSS compound, and 10 for a third POSS compound.

16. A method as set forth in claim 15 wherein the mixture consists essentially of the first, second, and third POSS compounds.

17. A method as set forth in claim 15 further comprising the step of separating one of the POSS compounds from the mixture via sublimation.

18. A method as set forth in claim 15 further comprising the step of reactivating the rhenium on cerium(IV) oxide after the mixture is formed.

19. A method as set forth in claim 18 wherein the step of reactivating occurs in a second reactor.

20. A method as set forth in claim 15 further comprising the step of adding an additional amount of the rhenium on cerium (IV) oxide to the reactor after the step of combining.

21. A method as set forth in claim 15 wherein the process is further defined as continuous and the reactor is further defined as a fluidized bed reactor.

* * * * *